United States Patent
Arakawa et al.

(10) Patent No.: US 6,377,836 B1
(45) Date of Patent: Apr. 23, 2002

(54) RF COIL ARRAY FOR VERTICAL FIELD MRI

(75) Inventors: Mitsuaki Arakawa, Hillsborough; Joseph W. Carlson, Kensington; Leon Kaufman; James V. Reveaux, both of San Francisco, all of CA (US)

(73) Assignee: Toshiba America MRI, Inc., Tustin, CA (US)

( * ) Notice: Subject to any disclaimer, the term of this patent is extended or adjusted under 35 U.S.C. 154(b) by 0 days.

(21) Appl. No.: 09/250,603

(22) Filed: Feb. 17, 1999

(51) Int. Cl.[7] ............................................... A61B 5/055
(52) U.S. Cl. ........................ 600/422; 324/318; 324/322
(58) Field of Search .................................. 600/422, 410; 324/318, 322

(56) References Cited

U.S. PATENT DOCUMENTS

| | | | |
|---|---|---|---|
| 4,594,566 A | | 6/1986 | Maudsley |
| 5,023,554 A | | 6/1991 | Cho et al. |
| 5,293,519 A | | 3/1994 | Yoshino et al. |
| 5,327,898 A | * | 7/1994 | Yoshino et al. ........... 128/653.5 |
| 5,351,688 A | * | 10/1994 | Jones ....................... 128/653.5 |
| 5,357,958 A | * | 10/1994 | Kaufman ................. 128/653.2 |
| 5,363,845 A | * | 11/1994 | Chowdhury et al. ..... 128/653.5 |
| 5,382,903 A | | 1/1995 | Young |
| 5,389,880 A | | 2/1995 | Mori |
| 5,394,087 A | | 2/1995 | Molyneaux |
| 5,416,413 A | * | 5/1995 | Leussler ..................... 324/318 |
| 5,430,378 A | | 7/1995 | Jones |
| 5,457,386 A | | 10/1995 | Matsunaga et al. |
| 5,500,596 A | | 3/1996 | Grist et al. |
| 5,510,714 A | | 4/1996 | Takahashi et al. |
| 5,519,321 A | | 5/1996 | Hagen et al. |
| 5,543,710 A | * | 8/1996 | Jones ........................ 324/318 |
| 5,592,088 A | * | 1/1997 | Matsunaga et al. ......... 324/318 |
| 5,602,557 A | | 2/1997 | Duerr |
| 5,699,802 A | | 12/1997 | Duerr |
| 5,929,639 A | * | 7/1999 | Doty ........................... 324/318 |
| 5,951,474 A | * | 9/1999 | Matsunaga et al. ......... 600/422 |
| 6,144,203 A | * | 11/2000 | Richard et al. ............ 324/318 |

OTHER PUBLICATIONS

Molyneaux, David A. et al., "Increased Signal to Noise Ratio Effects of the Arbitrary Placement Element", ISMRM Meeting in Australia, 1998.

* cited by examiner

Primary Examiner—Marvin M. Lateef
Assistant Examiner—Eleni Mantis Mercader
(74) Attorney, Agent, or Firm—Nixon & Vanderhye PC

(57) ABSTRACT

An RF coil array arrangement for enhanced magnetic resonance imaging of the breast or spine regions of prone and supine patients within a vertically oriented $B_0$ field is disclosed. Several RF coil array embodiments are disclosed that provide for both generating a nuclei nutation field pulse and acquiring nuclear magnetic resonance signals when functioning in an MRI apparatus environment that employs a vertical main magnetic field. A coil array may include one or more RF coils that are intended to be oriented such that their primary B field direction(s) are perpendicular to the vertical magnetic field of the MRI apparatus. Each coil array may further include one or more single loop or solenoidal coil(s) that are oriented having their central or longitudinal axis aligned parallel to the vertical main magnetic field so as to make advantageous use of non-axial field components associated with the coil(s) to further generate and receive desired NMR signal components.

17 Claims, 4 Drawing Sheets

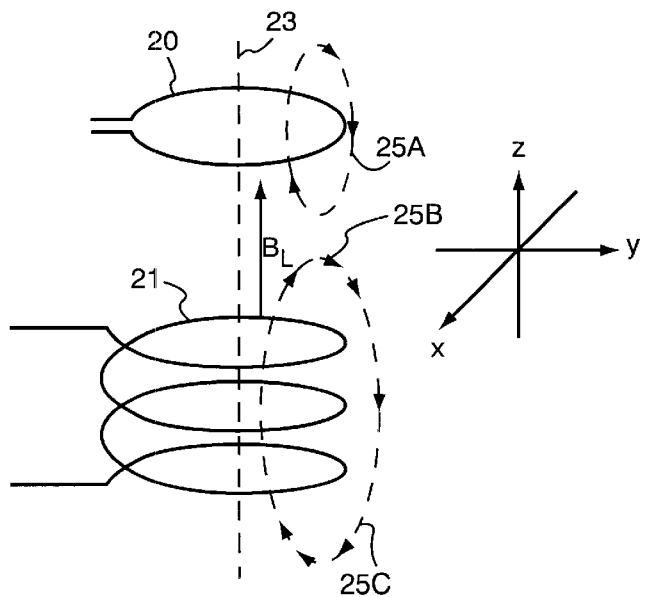
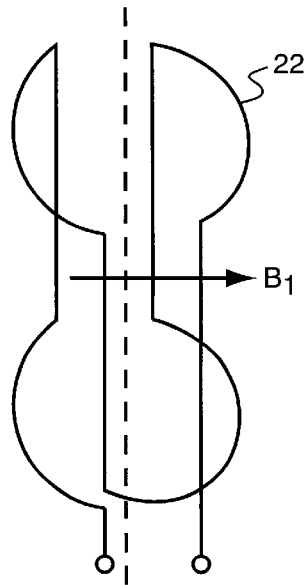
Fig.2A    Fig.2B
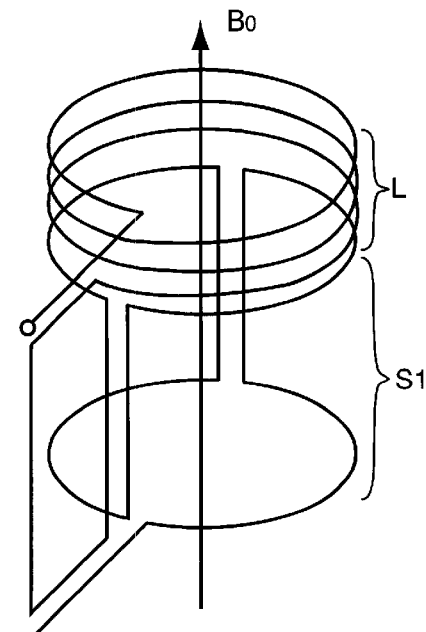
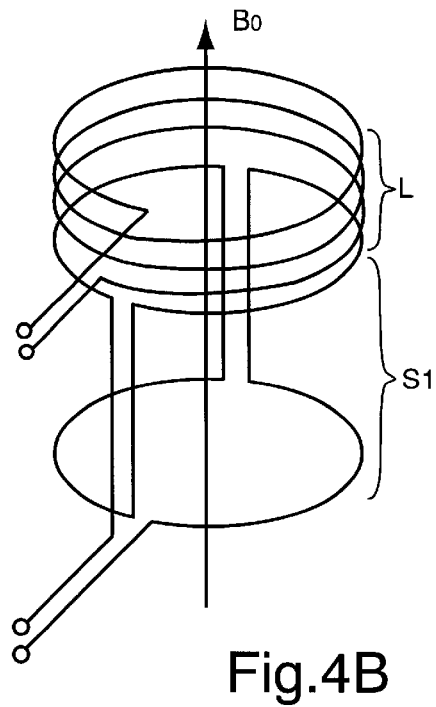
Fig.4A    Fig.4B

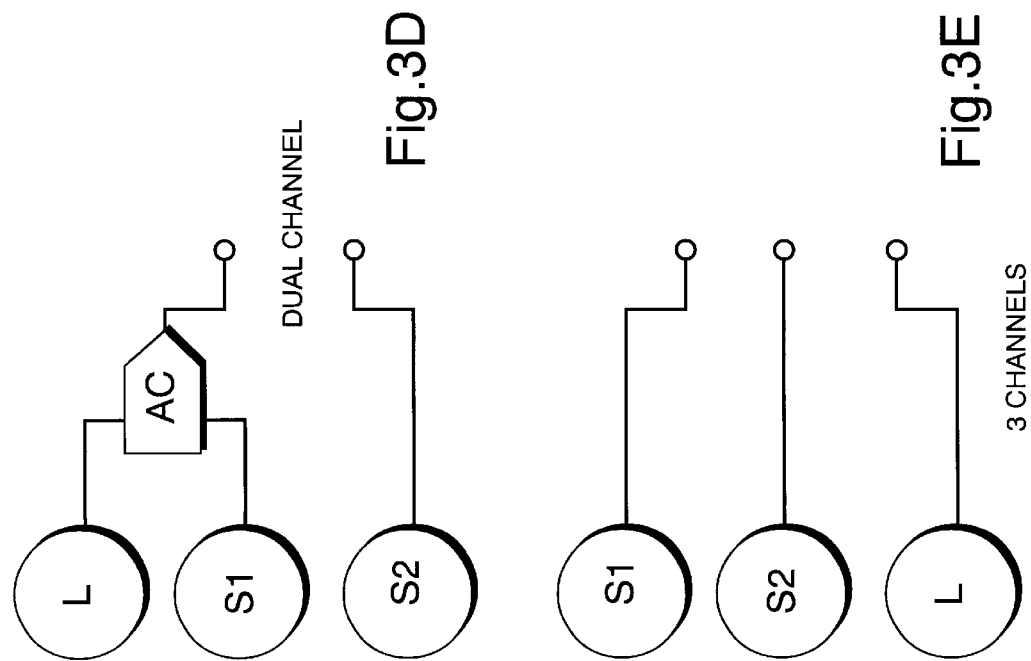
Fig.3D
Fig.3E
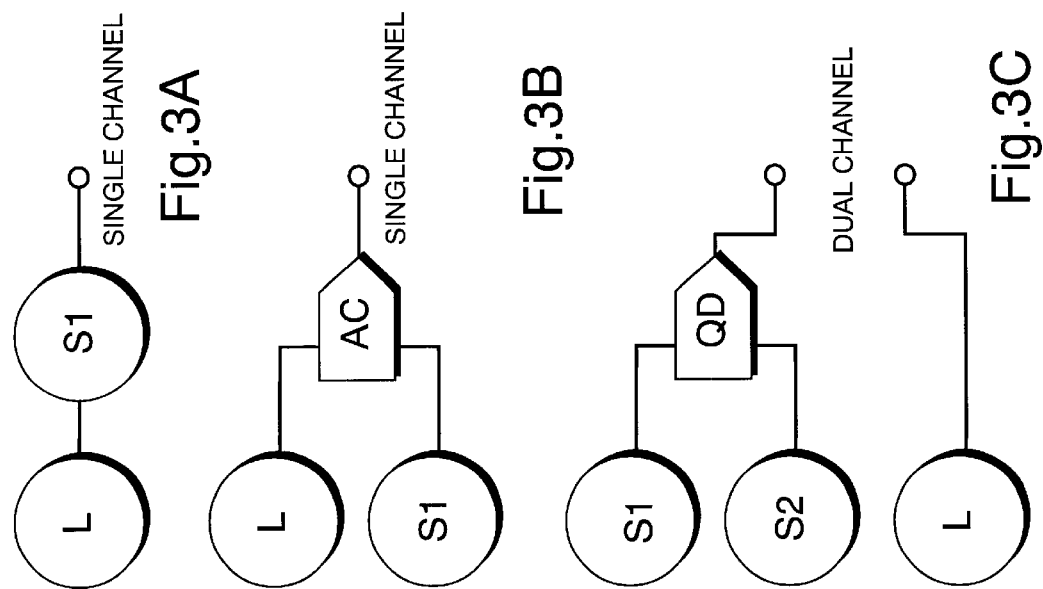
Fig.3A
Fig.3B
Fig.3C

RF COIL ARRAY FOR VERTICAL FIELD MRI

FIELD OF THE INVENTION

This invention relates generally to methods and apparatus for magnetic resonance imaging (MRI). In particular, it relates to radio frequency (RF) coil arrangements for generating the nuclei nutation field pulse and acquiring RF magnetic resonance signals when using an MRI apparatus that employs a vertical main magnetic field.

BACKGROUND OF THE INVENTION

Magnetic Resonance Imaging (MRI) has become a widely accepted and commercially viable technique for obtaining digitized visual images representing the internal structure of objects (such as the human body) having substantial populations of atomic nuclei that are susceptible to nuclear magnetic resonance (NMR) phenomena. In MRI, nuclei in an object to be imaged are polarized by imposing a strong static main magnetic field, $B_0$, on the nuclei. Selected nuclei are then excited (nutated) by imposing a radio frequency (RF) signal at a particular NMR frequency. By spatially encoding the selected nutated nuclei through a gradating of localized magnetic fields, and then suitably analyzing the resulting RF responses from the nuclei, a map or image of relative NMR responses as a function of the location of the nuclei can be determined. Following a Fourier analysis, data representing the NMR responses in space can be displayed on a CRT.

Commonly-known data acquisition techniques in MRI typically involve the utilization of localized RF receivers for acquiring NMR signals over a selected relatively small region of tissue. Conventional teachings suggest that efficient NMR signal reception requires the use an RF antenna coil configuration that has its greatest sensitivity in a direction that is substantially perpendicular to the main static magnetic field $B_0$ of the MRI apparatus. An example of such localized NMR signal receivers are the conventional type of conductive loop antennae that are often used for imaging, for example, the spine of a supine patient (i.e. reclining face up) or the breast of a prone patient (i.e., reclining face down) laying within a horizontal main static magnetic field. In the case of human breast examinations, it is often desirable to obtain NMR signals from a tissue area that extends somewhat into the body or chest wall at the base of the breast. Through empirical trials it has been determined by the inventors that a loop or solenoid type coil disposed at the base of the breast most advantageously provides the desired signal components in such situations.

For example, a technique to image the breast of a patient is for the patient to lie prone and allow the breast to hang freely into a multiple loop or solenoid-type signal receiver coil. In this way, the breast axis is maintained vertical and the solenoidal coil form may conveniently be used to surround and secure the breast tissues during imaging. Since the primary magnetic field of a solenoid coil lies along its longitudinal axis, its greatest sensitivity to RF signals lies along this same direction. Accordingly, a solenoidal coil for breast imaging has the advantage that when imaging is performed in a MRI system having a horizontal main magnetic field, the direction of greatest sensitivity of the solenoidal coil is aligned vertically—i.e., perpendicular to the main magnetic field—thereby allowing the coil to receive adequate MR signal levels from the chest wall of a prone patient.

When utilizing a MRI apparatus that employs a vertical main magnetic field, a "saddle" coil or a quadrature detection (QD) saddle coil pair is used for imaging breast tissues on a prone patient. This is because the saddle coil produces the majority of its magnetic field flux and has its greatest sensitivity in a direction perpendicular to its longitudinal—axis which in the above case of breast imaging on a prone patient would be aligned with the vertical main magnetic field. However, the magnetic field produced by a saddle coil does not extend sufficiently beyond the axial ends of the coil to significantly penetrate the chest wall. Consequently, it is usually not feasible to use a saddle coil or a QD saddle coil pair to obtain significant imaging data for tissue regions within the chest wall when imaging the breast in a vertical main field MRI apparatus.

Conventionally, a loop-type coil or a solenoidal coil is not oriented with its central axis oriented substantially parallel to the main static field of an MRI apparatus. It was conventionally anticipated that the NMR signal sensitivity of this type of coil would be at its lowest when its central axis is aligned parallel with the main field. Consequently, one would not have considered using a single loop coil or a solenoidal type coil for performing breast examinations on a prone subject in a MRI apparatus employing a vertical main magnetic field. Although the central $B_1$ field of a loop or solenoidal coil may well be vertical, and thus give rise to no magnetization signal (NMR signals) from tissue regions within the coil (i.e., because the field inside the coil is parallel to the static main magnetic field $B_0$), there are nevertheless substantial return flux field lines associated with a loop or solenoidal coil that lie beyond the axial end of the loop or solenoid which are directed at substantial angles—including perpendicular—to the background $B_0$ main field. The present invention developed from the inventors' recognition that in such situations, these "off axis" effects associated with coil conductors can be put to productive use in an axial $B_0$ field environment by allowing the production of a magnetization signal in tissue regions beyond the axial end of the coil.

In accordance with the present invention, productive use is made of the off axis effects associated with a loop or solenoidal coil(s) that is used in combination, for example, with one or more saddle coils in an RF coil array for NMR imaging. More specifically, the RF coils of such a multi-coil array are configured so that the longitudinal axes of the saddle coils are substantially parallel to the central axis of the loop (or solenoid) coil(s). The array is oriented within the imaging area of the MRI apparatus such that the central axis of the loop (or solenoid) coil is substantially parallel to the main $B_0$ field. In this manner, the saddle coil(s) will elicit NMR signals from tissues within the coil array while the loop (or solenoid) coil elicits signals from tissue areas beyond the axial ends of the multi-coil array.

Although it is known to combine a saddle coil with a solenoidal coil in an RF coil array for MRI (see, for example, U.S. Pat. No. 5,293,519 to Yoshino et al. and U.S. Pat. No. 5,592,088 to Matsunaga et al.), such arrangements conventionally require that the loop or solenoidal coil(s) of the array be oriented with its central axis pointed perpendicular to the main magnetic field. Moreover, such known coil arrangements are physically designed to work only in this manner and are not suitable or adaptable for imaging the breast or spine in any other orientation or relation with respect to the main field.

Accordingly, one object of the present invention is to provide an efficient MW nutation/RF coil array arrangement specifically for use in vertical main field MRI systems and which is particularly suited for imaging regions of the breast extending into the chest in a prone patient or imaging the spine in a supine patient. A preferred embodiment contemplates an RF coil array arrangement comprising one or more RF coils that gather NMR signals in the conventional way—i.e., by having their primary B field direction(s) oriented perpendicular to the MRI apparatus vertical magnetic field—combined with one or more single loop or solenoidal coils included in the array that are oriented having the central (longitudinal) axis aligned parallel to the vertical main magnetic field so as to also make use of the non-axial off axis components of the coil(s) to generate and receive NMR signal components from an extended region of tissue beyond the axial ends of the multi-coil array.

SUMMARY OF THE INVENTION

The present invention provides novel RF coil array arrangements for improving the magnetic resonance imaging of the breast or spine regions in prone (or supine) patients in a vertically oriented $B_0$ field. The invention provides a method and apparatus for generating a nuclei nutation field pulse and for acquiring nuclear magnetic resonance signals when using an MRI apparatus that employs a vertical main magnetic field. In particular, the invention is directed toward a method and apparatus for utilizing the non-axial field components of an RF coil(s) to extend the imaging region during breast and spine image acquisitions in a vertical main field MRI system.

Accordingly, one embodiment of the present invention is an RF coil array for imaging a human breast in a vertical main field magnetic resonance imaging (MRI) apparatus. The coil array comprising a coaxial nested conductive coil pair consisting of a saddle coil connected in series with a loop-type or a solenoid-type coil. The loop or solenoidal coil is positioned at one axial end of the saddle coil. The central axis of the loop coil is oriented parallel to both a central longitudinal axis of the saddle coil and the vertical main magnetic field of the imaging apparatus.

Another embodiment of the invention is an RF coil array for magnetic resonance imaging (MRI) in a vertical main magnetic field imaging apparatus. The coil array comprises a coaxial nested conductive coil pair consisting of a saddle coil, a loop-type (or a solenoidal type) coil, and an analog combiner. The saddle coil is connected in an analog combiner arrangement with the solenoidal coil.

In a third embodiment of the present invention, an RF coil array includes a quadrature detection saddle coil pair used in combination with a loop-type or solenoidal coil to provide two signal channels. In a fourth embodiment of the present invention, an RF coil array includes a saddle coil and a loop-type (or solenoid-type) coil connected together in an analog combiner arrangement and used in combination with a second saddle coil to provide two signal channels. In a fifth embodiment of the present invention, an RF coil array employs a combination of a first saddle coil, a second saddle coil and a loop-type or solenoidal coil to provide three signal channels.

BRIEF DESCRIPTION OF THE DRAWINGS

The structure and operation of the present invention will be more fully understood by careful study of the following detailed description of the presently preferred embodiment with particular reference to the accompanying drawings, wherein:

FIGS. 2A and 2B are schematic diagrams respectively illustrating exemplary winding configurations for loop, solenoidal and saddle-type RF coils;

FIGS. 3A–3E are schematic block diagrams of RF coil array arrangements for use in a vertical main field MRI system in accordance with the present invention;

FIGS. 4A and 4B are representative wiring schematics of the series coil array arrangement of FIG. 3A.

DETAILED DESCRIPTION OF THE PRESENTLY PREFERRED EMBODIMENT

Figure 1:
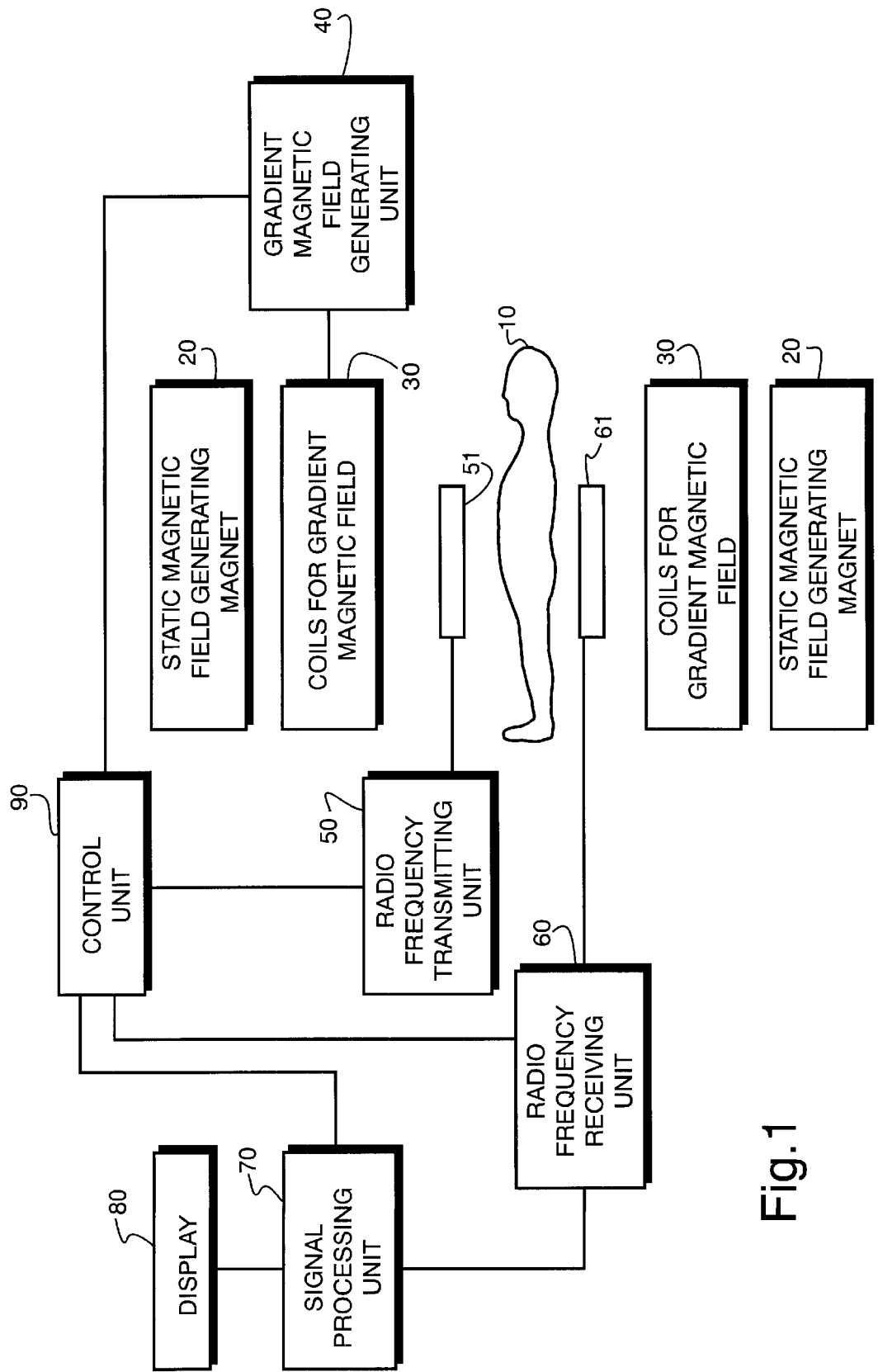
FIG. 1 is a general block diagram illustrating an example configuration of major components in a vertical main field MRI apparatus.

FIG. 1 depicts the general configuration of major components utilized in a conventional vertical main field MRI system. Typically, an MRI system for obtaining a transverse image of a patient 10 is composed of a superconducting coil magnet 20 for generating a large vertical static magnetic field, a coil arrangement 30 for producing large gradient magnetic fields. a gradient magnetic field pulse generating unit 40, a radio frequency transmitting unit 50 for producing an RF nutation pulse, a radio frequency receiving unit 60 for receiving NMR signals, a signal processing unit 70, a display device 80 and a control unit 90 for controlling operation and timing of all the associated units in the system.

The static main field generating magnet 20 is arranged in a space surrounding patient 10 and provides a powerful uniform vertical magnetic field through the patient. An output of the gradient magnetic field generating unit 40 is sent to the coil array 30 for producing three gradient magnetic fields $G_x$, $G_y$ and $G_z$ corresponding to X, Y and Z mutually orthogonal directions. A desired "slice" imaging plane through patient 10 can be selected through a controlled application of the three gradient magnetic fields. An RF pulse signal generated by radio frequency transmitting unit 50 is provided to RF coil 51 for transmitting an nuclei nutation pulse into the tissues of patient 10. The resulting radio frequency nuclear magnetic resonance (NMR) signals from patient 10 are detected by radio frequency receiving unit 60 after being picked-up by RF coil 61.

Other arrangements of coil 61 employs special RF coils that are movable and may be placed on or over a specific area of a patient's body. Alternatively, coil 61 may be part of a positional coil array as described in the one of the preferred embodiments of the present invention explained later.

Control unit 90 regulates the timing and application of the gradient magnetic fields and the transmission and reception of RF signals to RF coils 51 and 61, respectively. An NMR signal output from radio frequency receiving unit 60 is stored and subjected to Fourier transform analysis by signal processing unit 70 to produce image information for displaying on display unit 80.

FIGS. 2A and 2B respectively illustrate exemplary winding configurations for loop, solenoidal and saddle-type RF coils. Primary magnetic field $B_L$, for both single loop coil 20 and solenoid 21 coil, is generated along and parallel to the coil central axis 23. With saddle-type coil 22, the associated primary magnetic field $B_S$ is directed perpendicular to longitudinal axis 24. The loop and solenoid type coils also exhibit substantial off axis magnetic effects 25a, 25b and 25c that contain magnetic field components which are perpendicular to central axis 23. In accordance with the present invention, it is these off axis components 25a, 25b and 25c that are advantageously exploited in providing a coil array intended specifically for use in vertical main field MRI systems.

FIGS. 3A through 3E diagramatically illustrate coil type combinations for five exemplary RF coil array embodiments. FIG. 3A represents a first coil array embodiment comprising a single solenoidal (or loop) coil L connected in series with a saddle coil SI. This series connection arrangement of the two different coil types results in a single signal channel.

FIG. 3B illustrates a second coil array embodiment comprising a single saddle coil S1 connected in an analog combiner with a single solenoidal (or loop) coil L. In this embodiment, analog combiner AC combines signals from each coil to provide a single signal channel.

FIG. 3C illustrates a third coil array embodiment comprising a quadrature detection saddle-coil pair S1-S2 used in combination with solenoidal (or loop) coil L. In this embodiment, quadrature combiner QD combines signals from saddle coils S1 and S2 to provide a first signal channel. A solenoid (or loop) coil L, provides a second signal channel.

FIG. 3D illustrates a fourth coil array embodiment comprising a saddle coil S1 and solenoidal coil L connected together in an analog combiner arrangement and used in combination with a second saddle coil S2 to provide two signal channels. In this embodiment, analog combiner AC combines signals from saddle coil S1 and solenoid (or loop) coil L to provide a first signal channel. Saddle coil S2 provides a second signal channel.

FIG. 3E illustrates a fifth coil array embodiment comprising a first saddle coil S1 a second saddle coil S2 and a solenoid (or loop) coil L to provide three separate signal channels.

For each of the above disclosed coil array arrangements, the central (or longitudinal) axis of the loop (or solenoidal) coil is maintained parallel to the static main magnetic field $B_0$ of the MRI apparatus during use. For example, for imaging the breast and chest regions of a prone patient laying in a vertical $B_0$ field, an embodiment of the invention corresponding to the diagram of FIG. 3A may be used. For this embodiment, the coil array comprises a coaxial nested conductor coil pair consisting of a saddle coil connected in series with a solenoidal coil. Preferably, the loop (solenoidal) coil is nested with the saddle coil such that the central axis of the loop coil is coincident with the central longitudinal axis of the saddle coil and the loop coil is positioned at one axial end of the saddle coil, as represented by wiring schematics FIG. 4A or 4B. With this configuration, the coil array may be fitted over the breast of a prone patient laying in a vertical magnetic field MRI apparatus with the loop coil abutting against the chest of the patient, while the central axis of both the loop coil and the saddle coil remain aligned parallel to the vertical main magnetic field of the imaging apparatus.

The off axis magnetic components of the loop coil (e.g., 25a, 25b and 25c), which are perpendicular to central axis of the coil array and the vertical $B_0$ field, should be sensitive to nutation of nuclei within the chest wall to allow imaging of chest regions that would not be possible using a saddle coil alone. Alternatively, instead of being connected in series, the loop and saddle coil of the array of FIG. 4A or 4B could be arranged and connected to an analog combiner, as indicated by FIG. 3B.

Figure 5:
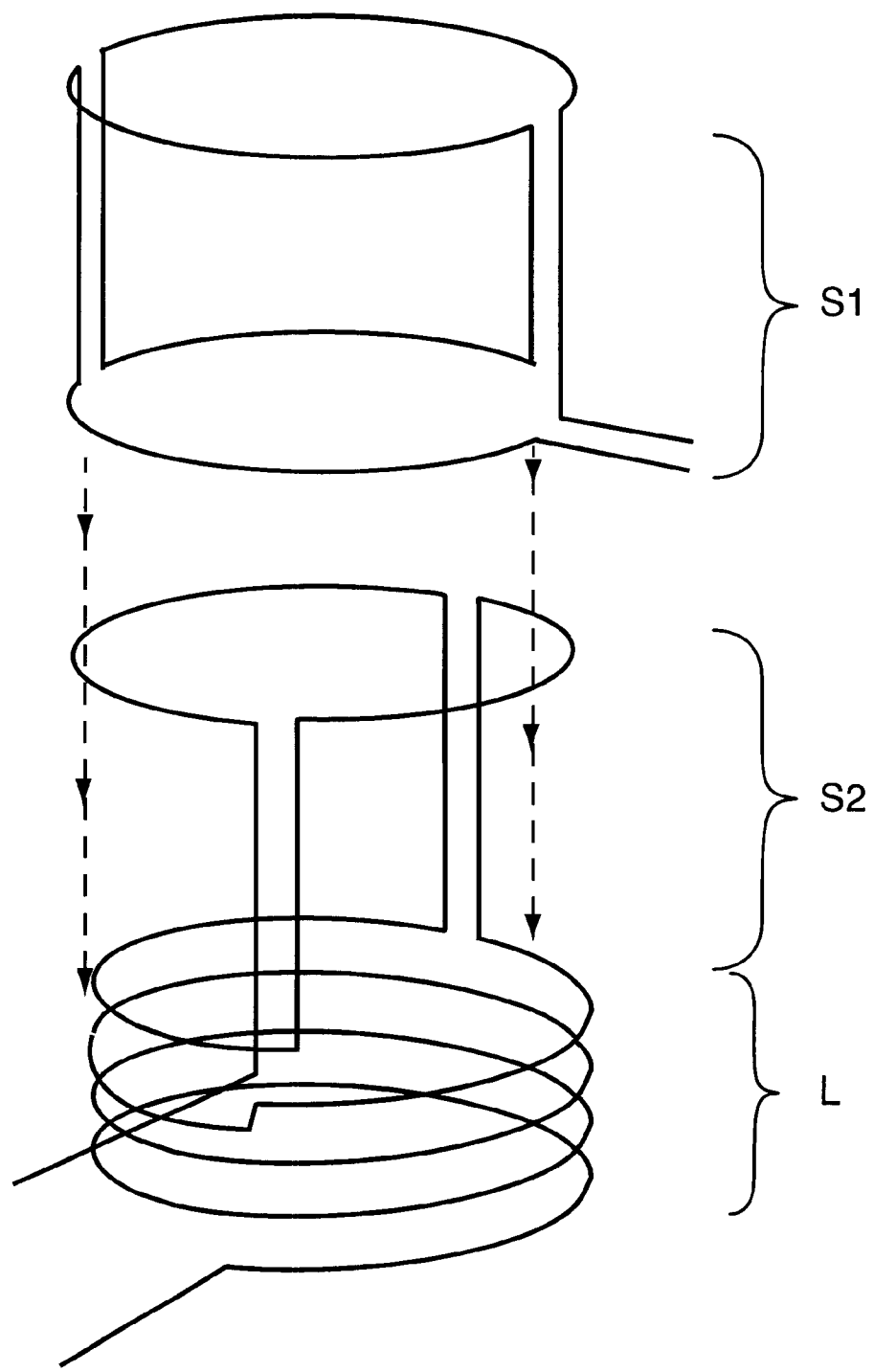
FIG. 5 is a representative wiring schematic of the three coil array arrangement of FIGS. 3B–3E.

In another embodiment for imaging the breast and chest regions of a prone patient laying in a vertical $B_0$ field, the coil array includes three coaxial nested coils comprising two saddle coils and a loop-type coil, as represented by wiring schematics FIG. 5A. With this arrangement, two coils are connected either in a quadrature (for two saddle coils) or an analog combine (for a saddle and a loop or solenoid coil) arrangement to provide one signal channel and the third coil used to provide a second channel or all three coils can be used separately to provide three signal channels, as represented by FIGS. 3C–3E.

While the invention has been described in connection with what is presently considered to be the mist practical and preferred embodiment(s), it is to be understood that the invention is not to be limited to the disclosed embodiment, but on the contrary, is intended to cover various modifications and equivalent arrangements included within the spirit and scope of the appended claims.

What is claimed is:

1. An RF coil array for use in imaging a human breast or other appendage and at least a portion of an adjoining torso region of a prone patient undergoing magnetic resonance imaging in a vertical main field magnetic resonance imaging (MRI) apparatus, the coil array comprising:

a coaxial nested conductive coil pair consisting of a saddle coil connected in series with a loop-type coil, wherein the loop-type coil is positioned coaxial with the saddle coil at one axial end of the saddle coil, and the central axis of the loop-type coil is oriented parallel to a main magnetic field of a vertical main magnetic field imaging apparatus.

2. An RF coil array as set forth in claim 1 wherein said loop-type coil is a solenoid coil.

3. An RF coil array arrangement for use in imaging a human breast or other appendage and at least a portion of an adjoining torso region of a prone patient undergoing magnetic resonance imaging in a vertical main field magnetic resonance imaging (MRI) apparatus, the coil array comprising:

a saddle coil;

a loop-type coil; and an analog combiner electrically connected between to the saddle coil and the loop-type coil, wherein the saddle coil is connected in an analog combiner arrangement with the loop-type coil and wherein the loop-type coil is positioned coaxial with the saddle coil at one axial end of the saddle coil and a central axis of the loop-type coil is oriented parallel to both a central longitudinal axis of the saddle coil and the vertical main magnetic field of the imaging apparatus.

4. An RF coil array as set forth in claim 3 wherein said loop-type coil is a solenoid coil.

5. An RF coil array for use in imaging a human breast or other appendage and at least a portion of an adjoining torso region of a prone patient undergoing magnetic resonance imaging (MRI) in a vertical main magnetic field imaging apparatus, the coil array comprising:

a first saddle coil;

a second saddle coil arranged coaxial with the first saddle coil to form a nested saddle coil pair;

a loop-type coil arranged coaxial with the first and second saddle coils; and a quadrature signal detector electrically connected between the first saddle coil and the second saddle coil, wherein said first and second saddle coils are connected in a quadrature detection arrangement and wherein the loop-type coil is positioned coaxial with the saddle coil pair at one axial end of the saddle coil pair and a central axis of the loop-type coil is oriented parallel to a vertical main magnetic field of the imaging apparatus.

6. An RF coil array as set forth in claim 5 wherein said loop-type coil is a solenoid coil.

7. An RF coil array for use in imaging a human breast or other appendage and at least a portion of an adjoining torso region of a prone patient undergoing magnetic resonance imaging (MRI) in a vertical main magnetic field imaging apparatus, the coil array comprising:

a first saddle coil;

a loop-type coil positioned coaxial with the first saddle coil at one axial end of the first saddle coil to form a nested coil pair;

a second saddle coil arranged coaxial with the nested coil pair; and an analog combiner electrically connected between the first saddle coil and the loop-type coil, wherein the first saddle coil and the loop-type coil are connected in an analog combiner arrangement and wherein a central axis of the loop-type coil is oriented parallel to a vertical main magnetic field of the imaging apparatus.

8. An RF coil array as set forth in claim 7 wherein said loop-type coil is a solenoid coil.

9. A three signal channel RF coil array for use in imaging a human breast or other appendage and at least a portion of an adjoining torso region of a prone patient undergoing magnetic resonance imaging (MRI) in a vertical main magnetic field imaging apparatus, the coil array comprising:

a first saddle coil;

a second saddle coil arranged coaxial with the first saddle coil to form a nested saddle coil pair; and a loop-type coil arranged coaxial with the first and second saddle coils, wherein the loop-type coil is positioned coaxial with the saddle coil pair at one axial end of the saddle coil pair and a central axis of the loop-type coil is oriented parallel to both a central longitudinal axis of the saddle coil pair and a vertical main magnetic field of the imaging apparatus.

10. An RF coil array as set forth in claim 9 wherein said loop-type coil is a solenoid coil.

11. A method for imaging a human breast or other appendage and at least a portion of an adjoining torso or chest region of a prone patient laying in a vertical main field magnetic resonance imaging (MRI) apparatus, comprising the steps of:

a) inserting a breast of said prone patient into an open axial end of an MRI coil array comprising a plurality of coaxial RF coil elements wherein at least one RF coil element is a loop-type coil and at least one RF coil element is a saddle coil, said MRI coil array surrounding the breast and oriented such that a loop-type coil of the array abuts against a chest region of the patient, said array configured such that the loop-type coil is positioned coaxial with a saddle coil at one axial end of the saddle coil and the central axis of the loop-type coil is oriented parallel to a main magnetic field of the vertical main magnetic field imaging apparatus; and b) using said MRI coil array during image acquisition for producing nuclei nutation and/or receiving nuclear magnetic resonance (NMR) signals, wherein substantial non-axial magnetic field components from the loop-type coil extend into chest tissue regions inaccessible by magnetic field components from a saddle coil element of the array.

12. A method for imaging a human breast and a chest region of a prone patient as set forth in claim 11 wherein said loop-type coil is a solenoid coil.

13. A method for imaging a human breast and a chest region of a prone patient as set forth in claim 11 wherein said MRI coil array consists of a loop-type coil connected in series with a saddle coil.

14. A method for imaging a human breast and a chest region of a prone patient as set forth in claim 11 wherein said MRI coil array consists of a saddle coil, a loop-type coil, and an analog combiner, wherein the saddle coil is connected in an analog combiner arrangement with the loop-type coil.

15. A method for imaging a human breast and a chest region of a prone patient as set forth in claim 11 wherein said MRI coil array consists of a first saddle coil, a second saddle coil, a loop-type coil and a quadrature signal detector electrically connected between the first saddle coil and the second saddle coil to provide two signal channels.

16. A method for imaging a human breast and a chest region of a prone patient as set forth in claim 11 wherein said MRI coil array consists of a first saddle coil, a second saddle coil, a loop-type coil and an analog combiner electrically connected between the loop-type coil and a saddle coil to provide two signal channels.

17. A method for imaging a human breast and a chest region of a prone patient as set forth in claim 11 wherein said MRI coil array consists of a first saddle coil, a second saddle coil and a loop-type coil to provide three signal channels.

* * * * *